United States Patent
Tsau et al.

(10) Patent No.: US 10,463,500 B2
(45) Date of Patent: Nov. 5, 2019

(54) MEDICAL COMPOSITE MATERIAL, METHOD FOR FABRICATING THE SAME AND APPLICATIONS THEREOF

(71) Applicant: INDUSTRIAL TECHNOLOGY RESEARCH INSTITUTE, Hsinchu (TW)

(72) Inventors: Fanghei Tsau, Kaohsiung (TW); Jibin Horng, Tainan (TW); Hsinhsin Shen, Hsinchu County (TW); Hongjen Lai, Hsinchu (TW); Chingchih Lin, Tainan (TW); Peiyi Tsai, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 470 days.

(21) Appl. No.: 14/585,894

(22) Filed: Dec. 30, 2014

(65) Prior Publication Data

US 2016/0128843 A1    May 12, 2016

(30) Foreign Application Priority Data

Nov. 7, 2014    (TW) .............................. 103138658 A (51) Int. Cl.
*A61F 2/44*    (2006.01)
*A61L 27/34*    (2006.01)
(Continued)

(52) U.S. Cl.
CPC .............. *A61F 2/442* (2013.01); *A61L 27/30* (2013.01); *A61L 27/34* (2013.01); *A61L 27/50* (2013.01);
(Continued)

(58) Field of Classification Search
CPC ....................................................... A61F 2/44
See application file for complete search history.

(56) References Cited

U.S. PATENT DOCUMENTS

| 3,868,229 A | 2/1975 | Hurley |
| 4,012,795 A | 3/1977 | Doore et al. |
(Continued)

FOREIGN PATENT DOCUMENTS

| CN | 101128166 A | 2/2008 |
| CN | 102574362 A | 7/2012 |
(Continued)

OTHER PUBLICATIONS

Taiwan Office Action dated Sep. 17, 2015 for Appl. No. 103141581.
(Continued)

*Primary Examiner* — Humera N Sheikh
*Assistant Examiner* — Xiaobei Wang
(74) *Attorney, Agent, or Firm* — Birch, Stewart, Kolasch & Birch, LLP (57) ABSTRACT

A medical composite material, a method for fabricating the same and applications thereof are disclosed, wherein the medical composite material includes an interface layer, a polymer layer and a metal layer. The interface layer has a first surface, a second surface opposite to the first surface and a plurality protrusion portions protruding outwards from the first surface, wherein each of the protrusion portions has an aspect ratio substantially ranging from 1 μm to 4000 μm. The polymer layer is conformally in contact with the first surface and the protrusion portions. The metal layer is in contact with the second surface.

11 Claims, 6 Drawing Sheets

(51) Int. Cl.
  *B32B 15/01* (2006.01)
  *A61L 27/56* (2006.01)
  *A61L 27/30* (2006.01)
  *A61L 27/50* (2006.01)
(52) U.S. Cl.
  CPC .......... *A61L 27/56* (2013.01); *A61L 2420/02* (2013.01); *A61L 2430/38* (2013.01)

(56) References Cited

U.S. PATENT DOCUMENTS

| | | |
|---|---|---|
| 4,411,943 A | 10/1983 | Akao |
| 4,483,786 A | 11/1984 | Johnson et al. |
| 4,642,163 A | 2/1987 | Greschner et al. |
| 5,201,766 A | 4/1993 | Georgette |
| 5,370,698 A | 12/1994 | Heimke et al. |
| 5,716,415 A * | 2/1998 | Steffee ................... A61F 2/447 623/17.16 |
| 5,879,398 A | 3/1999 | Swarts et al. |
| 6,074,740 A | 6/2000 | Scheckenbach et al. |
| 6,126,695 A | 10/2000 | Semlitsch |
| 6,602,293 B1 | 8/2003 | Biermann et al. |
| 6,800,073 B2 | 10/2004 | Palasis et al. |
| 7,060,056 B2 | 6/2006 | Palasis et al. |
| 7,189,409 B2 | 3/2007 | Pirhonen et al. |
| 7,285,331 B1 | 10/2007 | Reihs et al. |
| 7,875,075 B2 | 1/2011 | Schwab |
| 8,128,700 B2 | 3/2012 | Delurio et al. |
| 8,303,879 B2 | 11/2012 | Bertele et al. |
| 8,323,722 B2 | 12/2012 | Rabiei |
| 8,361,150 B2 | 1/2013 | Zhang et al. |
| 8,414,650 B2 | 4/2013 | Bertele et al. |
| 8,420,181 B2 | 4/2013 | Kim |
| 8,425,604 B2 | 4/2013 | Trieu |
| 8,470,042 B2 | 6/2013 | Zhang et al. |
| 8,603,174 B2 | 12/2013 | Haines |
| 9,522,820 B2 | 12/2016 | Khine et al. |
| 9,782,268 B2 | 10/2017 | Aeschlimann et al. |
| 2005/0037916 A1 | 2/2005 | Chen et al. |
| 2005/0049716 A1 | 3/2005 | Wagener et al. |
| 2005/0192675 A1 | 9/2005 | Robinson |
| 2006/0202385 A1 | 9/2006 | Xu et al. |
| 2007/0026197 A1 | 2/2007 | Suga et al. |
| 2008/0015616 A1 | 1/2008 | Ricci et al. |
| 2008/0107890 A1* | 5/2008 | Bureau ................. A61L 27/446 428/323 |
| 2008/0125510 A1 | 5/2008 | Crosby et al. |
| 2008/0157235 A1 | 7/2008 | Rogers et al. |
| 2009/0084491 A1 | 4/2009 | Uthgenannt et al. |
| 2009/0220561 A1 | 9/2009 | Jin et al. |
| 2009/0276053 A1 | 11/2009 | Brown et al. |
| 2010/0023057 A1 | 1/2010 | Aeschlimann et al. |
| 2010/0062590 A1 | 3/2010 | Lin et al. |
| 2010/0082067 A1 | 4/2010 | Kondrashov |
| 2010/0092754 A1 | 4/2010 | Nishida et al. |
| 2010/0137990 A1 | 6/2010 | Apatsidis et al. |
| 2010/0256773 A1 | 10/2010 | Thijs et al. |
| 2010/0262244 A1* | 10/2010 | Savage-Erickson .... A61F 2/442 623/17.16 |
| 2010/0304065 A1* | 12/2010 | Tomantschger ........ B32B 15/08 428/35.8 |
| 2011/0039086 A1 | 2/2011 | Graham et al. |
| 2011/0060399 A1 | 3/2011 | Charlebois |
| 2011/0125284 A1 | 5/2011 | Gabbrielli et al. |
| 2011/0153028 A1 | 6/2011 | Albertorio |
| 2011/0287203 A1 | 11/2011 | Victor et al. |
| 2012/0010599 A1 | 1/2012 | Jin et al. |
| 2012/0187406 A1 | 7/2012 | Tsai et al. |
| 2012/0221110 A1 | 8/2012 | Nakanishi et al. |
| 2012/0277861 A1 | 11/2012 | Steele et al. |
| 2012/0277869 A1 | 11/2012 | Siccardi et al. |
| 2013/0030529 A1 | 1/2013 | Hunt |
| 2013/0096689 A1 | 4/2013 | Lowry et al. |
| 2013/0119487 A1 | 5/2013 | Lin et al. |
| 2013/0131699 A1 | 5/2013 | Jiang et al. |
| 2013/0131824 A1 | 5/2013 | Meehan et al. |
| 2013/0166028 A1 | 6/2013 | Shieh et al. |
| 2013/0218288 A1 | 8/2013 | Fonte et al. |
| 2014/0302279 A1 | 10/2014 | Pfaffelhuber et al. |
| 2014/0363631 A1 | 12/2014 | Gong et al. |
| 2015/0012100 A1 | 1/2015 | Ullrich, Jr. et al. |
| 2015/0093717 A1 | 4/2015 | Ali |
| 2016/0135958 A1 | 5/2016 | Grostefon et al. |
| 2016/0155537 A1 | 6/2016 | Manabe et al. |

FOREIGN PATENT DOCUMENTS

| | | |
|---|---|---|
| CN | 202617335 U | 12/2012 |
| CN | 103200887 A | 7/2013 |
| CN | 103242561 A | 8/2013 |
| CN | 104921645 A | 9/2015 |
| CN | 206167016 U | 5/2017 |
| EP | 1 175 949 A1 | 1/2002 |
| EP | 2 435 602 A1 | 4/2012 |
| EP | 2 641 621 A1 | 9/2013 |
| EP | 2 526 977 B1 | 2/2014 |
| EP | 2 762 172 A1 | 8/2014 |
| JP | 5-131005 A | 5/1993 |
| JP | 2011-143539 A | 7/2011 |
| TW | 280767 B | 7/1996 |
| TW | 200708295 A | 3/2007 |
| TW | I302372 B | 10/2008 |
| TW | 200902610 A | 1/2009 |
| TW | I321372 B | 3/2010 |
| TW | I346253 B | 8/2011 |
| TW | 201232783 A | 8/2012 |
| TW | M438893 U1 | 10/2012 |
| TW | I376734 B | 11/2012 |
| TW | 201249392 A1 | 12/2012 |
| TW | 201320331 A | 5/2013 |
| TW | I423782 B | 1/2014 |
| TW | I448270 B | 8/2014 |
| WO | WO 2006/063354 A1 | 6/2006 |
| WO | WO 2012/110816 A1 | 8/2012 |
| WO | WO 2014/072983 A1 | 5/2014 |

OTHER PUBLICATIONS

Achour et al., "Stress Distribution in Dental Implant with Elastomeric Stress Barrier", Materials and Design, vol. 32, 2011, pp. 282-290.
Amanat et al. "Gas Permeability Reduction in PEEK Film: Comparison of Tetrahedral Amorphous Carbon and Titanium Nanofilm Coatings", Journal of Membrane Science, vol. 378, 2011 pp. 265-271.
Breguet et al., "Compact, Light Weight Mechanisms for High Precision Micro-Manipulators", Swiss Federal Institute of Technology Lausanne (EPFL), Switzerland, Sep. 1999, 5 pages.
Chen et al., "Numerical Simulation of Two-Dimensional Melting and Resolidification of a Two-Component Metal Powder Layer in Selective Laser Sintering Process", Numerical Heat Transfer, Part A, vol. 46, 2004, pp. 633-649.
Chen et al., "Three-Dimensional Modeling of Laser Sintering of a Two-Component Metal Powder Layer on Top of Sintered Layers", Journal of Manufacturing Science and Engineering, vol. 129, Jun. 2007, pp. 575-582.
Contuzzi et al., "3D Finite Element Analysis in the Selective Laser Melting Process", Int J Simul Model, vol. 10, No. 3, 2011, pp. 113-121.
Devine et al. "Coating of Carbon Fiber-Reinforced Polyetheretherketone Implants with Titanium to Improve Bone Apposition", Society for Biomaterials, Published online Dec. 20, 2012, pp. 591-598.
Du et al., "Plastic Forming Simulations of Cold Isostatic Pressing of Selective Laser Sintered Components", Transactions of Nonferrous Metals Society of China, vol. 21, 2011, pp. 1118-1122.
Facchini et al., "Ductility of a Ti—6Al—4V Alloy Produced by Selective Laser Melting of Prealloyed Powders", Rapid Prototyping Journal, vol. 16, No. 6, 2010, pp. 450-459, plus 3 additional pages.
Fan et al., "Numerical Modeling of the Additive Manufacturing (AM) Processes of Titanium Alloy", Titanium Alloys—Towards (56) References Cited

OTHER PUBLICATIONS

Achieving Enhanced Properties for Diversified Applications, Intech, Published Online Mar. 16, 2012 (Published in Print Mar. 2012), pp. 3-28, plus cover page.
Han et al., "Fabrication of Gear Having Functionally Graded Properties by Direct Laser Melting Process", Advances in Mechanical Engineering, vol. 2014, Article ID 618464, published Apr. 9, 2014, pp. 1-6, plus 1 additional page.
Han et al., "The Electron Beam Deposition of Titanium on Polyetheretherketone (PEEK) and the Resulting Enhanced Biological Properties", Biomaterials, vol. 31, 2010, pp. 3465-3470.
Hsu et al., "Parametric Study on the Interface Pullout Strength of the Vertebral Body Replacement Cage Using FEM-Based Taguchi Methods", Medical Engineering & Physics, vol. 31, 2009, pp. 287-294.
Kolossov et al., "3D FE Simulation for Temperature Evolution in the Selective Laser Sintering Process", International Journal of Machine Tools & Manufacture, vol. 44, 2004, pp. 117-123.
Laurens et al., "Enhancement of the Adhesive Bonding Properties of PEEK by Excimer Laser Treatment", International Journal of Adhesion & Adhesives, vol. 18, 1998, pp. 19-27.
Lin et al., "Structural and Mechanical Evaluations of a Topology Optimized Titanium Interbody Fusion Cage Fabricated by Selective Laser Melting Process", Journal of Biomedical Materials Research, vol. 83, Part A, 2007, Published Online Apr. 5, 2007, pp. 272-279.
Maurer et al., "Erosion Resistant Titanium Based PVD Coatings on CFRP", Wear, vol. 302, 2013, pp. 937-945.
Mikos et al., "Laminated Three-Dimensional Biodegradable Foams for Use in Tissue Engineering", Biomaterials, vol. 14, No. 5, 1993, pp. 323-330.
Roberts et al., "A Three-Dimensional Finite Element Analysis of the Temperature Field During Laser Melting of Metal Powders in Additive Layer Manufacturing", International Journal of Machine Tools & Manufacture, vol. 49, 2009, pp. 916-923.
Seyda et al., "Investigation of Aging Processes of Ti—6Al—4V Powder Material in Laser Melting", Physics Procedia, vol. 39, 2012, pp. 425-431.
Sumner et al., "Functional Adaptation and Ingrowth of Bone Vary as a Function of Hip Implant Stiffness", Journal of Biomechanics, vol. 31, 1998, pp. 909-917.
Wu et al. "Investigation of Hydroxyapatite Coated Polyether Ether Ketone Composites by Gas Plasma Sprays", Surface & Coatings Technology, vol. 203, 2009, pp. 2755-2758.
Wu et al., "Porous Titanium-6 Aluminum-4 Vanadium Cage Has Better Osseointegration and Less Micromotion Than a Poly-Ether-Ether-Ketone Cage in Sheep Vertebral Fusion", Artificial Organs, vol. 37, No. 12, 2013, pp. E191-E201.
Xiao et al., "Topology Optimization of Microstructure and Selective Laser Melting Fabrication for Metallic Biomaterial Scaffolds", Transactions of Nonferrous Metals Society of China, vol. 22, 2012, pp. 2554-2561.
Zhong et al., "Finite Element Analysis of the Lumbar Spine with a New Cage Using a Topology Optimization Method", Medical Engineering & Physics, vol. 28, 2006, pp. 90-98.
Taiwanese Office Action and Search Report for Taiwanese Application No. 104140981, dated Feb. 18, 2017.
Taiwanese Office Action and Search Report for Taiwanese Application No. 104142314, dated Mar. 15, 2017.
U.S. Office Action for U.S. Appl. No. 14/586,171, dated Dec. 30, 2016.
U.S. Office Action for U.S. Appl. No. 14/586,171 dated Jun. 15, 2016.
U.S. Office Action for U.S. Appl. No. 14/981,325, dated Sep. 26, 2017.
UL Prospector, "Polyaryletherketone (PAEK) Typical Properties Generic PEEK," Data Sheet, URL: https://plastics.ulprospector.com/generics/29/c/t/polyaryletherketone-paek-properties-processing/sp/4, Obtained on Sep. 20, 2017, pp. 1-2.
U.S. Office Action for U.S. Appl. No. 14/586,171, dated Dec. 28, 2017.
U.S. Office Action for U.S. Appl. No. 14/977,234, dated Dec. 26, 2017.
U.S. Office Action for U.S. Appl. No. 14/981,325, dated Feb. 14, 2018.
Taiwanese Office Action dated Jun. 1, 2018 for TW Application No. TW 106128720.
U.S. Office Action dated Jul. 13, 2018 for U.S. Appl. No. 14/586,171.

* cited by examiner

MEDICAL COMPOSITE MATERIAL, METHOD FOR FABRICATING THE SAME AND APPLICATIONS THEREOF

This application claims the benefit of Taiwan application Serial No. 103138658, filed Nov. 7, 2014, and the subject matter of which is incorporated herein by reference.

TECHNICAL FIELD

The technical field relates in general to a medical composite material, method for fabricating the same and applications thereof.

BACKGROUND

Ideal medical material should be capable of being tightly bonded with tissues and applicable to complicated structure to strengthen the critical design of specific parts. However, most of existing implantable medical products are formed of one single material. Let the orthopedic products, such as bone screws, spinal fixation device, inter-body fusion device, artificial disk, and artificial joints that are implanted into bone tissues, be taken for example. Most of the orthopedic products are formed of one single material, such as a metal or a biomedical polymer material.

In respect of the applicableness of the material and the compatibility between the material and human bone tissues, although metal material has excellent strength of support and osseo-integration, stress shielding effect may still occurs at normal bone tissue interface due to the huge difference between the elastic modulus and bone tissues and cause bone tissue structure to collapse. Biomedical polymer material that is characterized as a bio-inert and hydrophobic material lacking the function of inducing bone cells to grow and attach thereon cannot be easily fused with bone cells and has the risk of pull out the bone tissues, despite having an elastic modulus similar to human bone tissues and being capable of reducing the stress shielding effect through suitable distribution of stress to avoid the collapse and loss of bone tissues.

Therefore, a medical composite material method for fabricating the same and applications thereof are required for resolving the problems encountered in generally known technology.

SUMMARY

The embodiments of the disclosure are directed to a medical composite material with hetero-junction, and a manufacturing method and applications thereof. According to one embodiment of the disclosure, a medical composite material comprising an interface layer, a polymer layer and a metal layer is disclosed. The interface layer has a first surface, a second surface opposite to the first surface and a plurality of protrusion portions protruding from the first surface, wherein each protrusion portion has an aspect ratio substantially ranging from 1 μm to 4000 μm. The polymer layer is conformally in contact with the first surface and the protrusion portions. The metal layer is in contact with the second surface.

According to another embodiment of the disclosure, a method for fabricating a medical composite material is disclosed. The manufacturing method comprises steps as follows. Firstly, a polymer layer is provided. Next, an interface layer is formed on the polymer layer, wherein the interface layer has a first surface and a second surface opposite to the first surface. The first surface is conformally in contact with the polymer layer and has a plurality of protrusion portions each extending into the polymer layer and having an aspect ratio substantially ranging from 1 μm to 4000 μm. Then, a metal layer is formed on the second surface.

According to yet another embodiment of the disclosure, an inter-body fusion device formed of the said medical composite material is disclosed.

BRIEF DESCRIPTION OF THE DRAWINGS

The above and other aspects of the invention will become better understood with regard to the following detailed description of the preferred but non-limiting embodiment (s). The following description is made with reference to the accompanying drawings.

FIG. 1 is a flowchart of a method for fabricating a medical composite material according to an exemplary embodiment;

FIG. 1A to FIG. 1D are structural cross-sectional views of the method for fabricating a medical composite material according to FIG. 1;

FIG. 2 is a perspective of a metal mesh structure of a metal layer formed of the medical composite material according to an exemplary embodiment;

FIG. 3A is a 3D structural perspective of an inter-body fusion device using the medical composite material according to an exemplary embodiment;

FIG. 3B is a structural explosion diagram of the inter-body fusion device of FIG. 3A; and FIG. 4 is a structural diagram of the inter-body fusion device of FIG. 3 used in human vertebra according to an exemplary embodiment.

DETAILED DESCRIPTION

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

The embodiments disclosed in the present specification relate to a medical composite material, a method for fabricating the same and applications thereof capable of resolving the problems derived from the stress shielding effect which occurs when the medical material used in a conventional technology is formed of one single material. For the above objects, features and advantages of the present invention to be clearly understood, a method for fabricating a medical composite material with hetero-junction, and an inter-body fusion device using the medical composite material formed by the method fabricating the medical composite material with hetero-junction are disclosed in an exemplary embodiment, and detailed descriptions are disclosed below with accompanying drawings.

Figure 1:
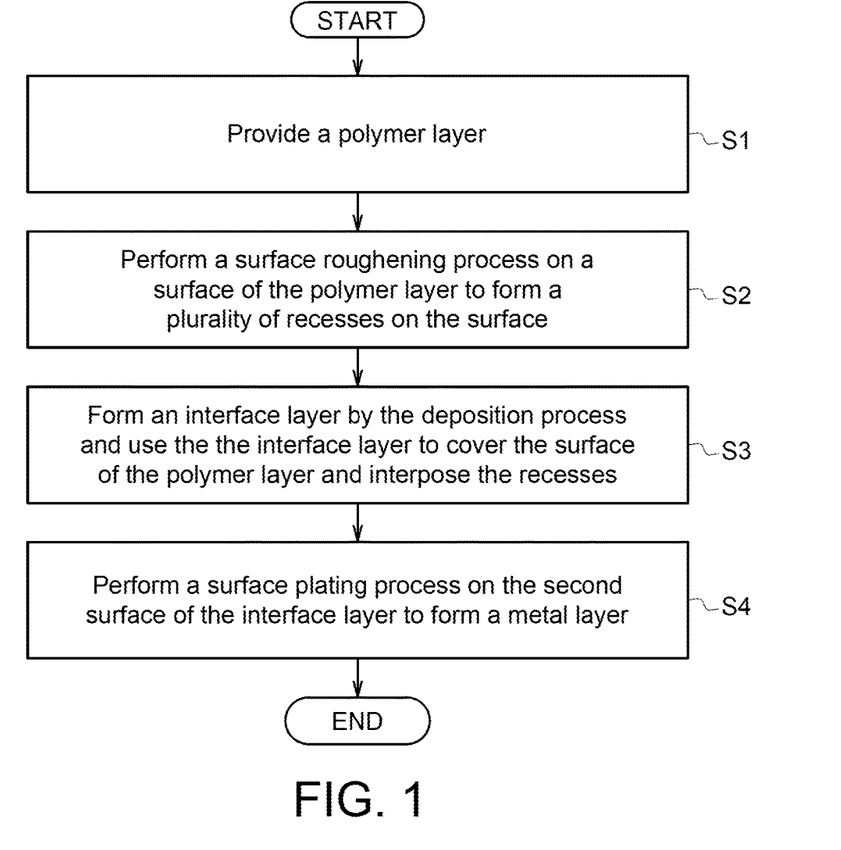
Figure 1A:
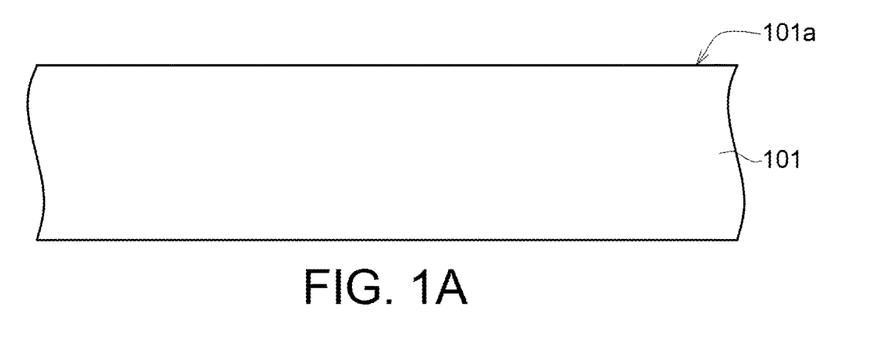

FIG. 1 is a flowchart of a method for fabricating a medical composite material 100 according to an embodiment of the present invention. FIG. 1A to FIG. 1D are structural cross-sectional views of the method for fabricating a medical composite material 100 of FIG. 1. Firstly, the method for fabricating the medical composite material 100 begins at step S1, a polymer layer 101 is provided (as indicated in FIG. 1A).

The polymer layer 101 can be formed of a polymer compound using a plasticized polymer such as plastic, silicone, synthetic rubber, synthetic fibers, synthetic paint or adhesive as the base, or a natural polymer compound comprising cellulose, starch, and protein.

In some embodiments of the present invention, the polymer layer 101 can be formed by performing injection molding, pultrusion, membrane pressing, thermal pressing, blow molding, molding, filament winding, prepreg material laminating, transferring, foaming, casting, or lamination on a thermoplastic plastic, such as polyethylene (PE), polypropylene (PP), polystyrene (PS), polymethyl methacrylate (PMMA), polyvinyl chloride (PVC), nylon (Nylon), polycarbonate (PC), polyurethane (PU), polytetrafluoroethylene (PTFE), polyethylene terephthalate (PET, PETE), or a thermosetting plastic, such as epoxy, phenolic, polyimide, melamine formaldehyde resin.

In the present embodiment, the polymer layer 101 is formed of a polymer comprising polyether ether ketone (PEEK), carbon reinforced (PEEK), polyetherketoneketone (PEKK), polyaryletherketone (PAEK) or a combination thereof. The properties of the polymer layer 101 are similar to that of human bones. For example, the polymer layer 101 has an elastic modulus substantially ranging from 2 Gpa to 22 Gpa.

It should be noted that the polymer layer 101 used in the present invention is not limited thereto, and any polymer materials suitable for contacting biological tissues are within the spirit of the present invention. In some embodiments, the polymer layer 101 can be formed of other polymer materials according to the biological properties of the biological tissue to which the medical composite material 100 is applied.

Figure 1B:
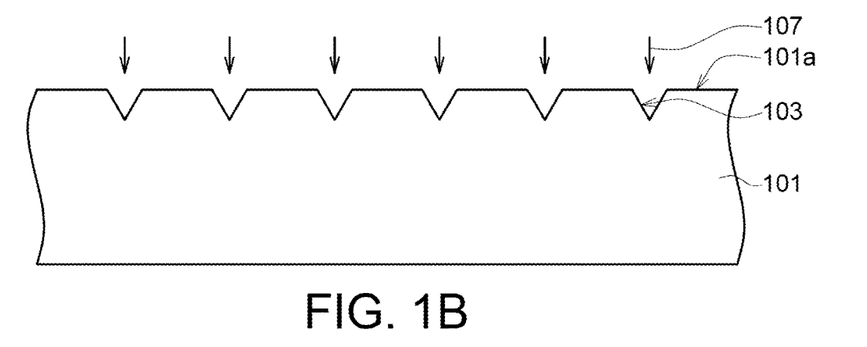

In step S2, a surface roughening process 107 is performed on a surface 101a of the polymer layer 101 to form a plurality of recesses 103 on the surface 101a, wherein each recess 103 has an aspect ratio substantially ranging from 1 µm to 4000 µm (as indicated in FIG. 1B). In some embodiments of the present invention, the surface roughening process 107 removes a part of the polymer layer 101 by way of CNC processing, laser surface treatment, plasma surface treatment, etching or a combination thereof to form a plurality of openings or grooves (recesses 103) extending into the polymer layer 101 from the surface 101a.

During the surface roughening process 107 of the present embodiment, a laser light with a pulse width less than 1 nanosecond (ns) is used to radiate the polymer layer 101, whereby a plurality of micro-structures having controllable and uniform dimensions are formed on the surface 101a of the polymer layer 101. The micro-structures are formed as an array pattern composed of a plurality of recesses 103 each having an aspect ratio ranging from 1 µm to 4000 µm. However, the arrangement of micro-structures is not limited thereto. For example, in some embodiments of the present invention, the micro-structures are an irregular pattern composed of a plurality of recesses 103 arranged in an irregular manner.

Figure 1C:
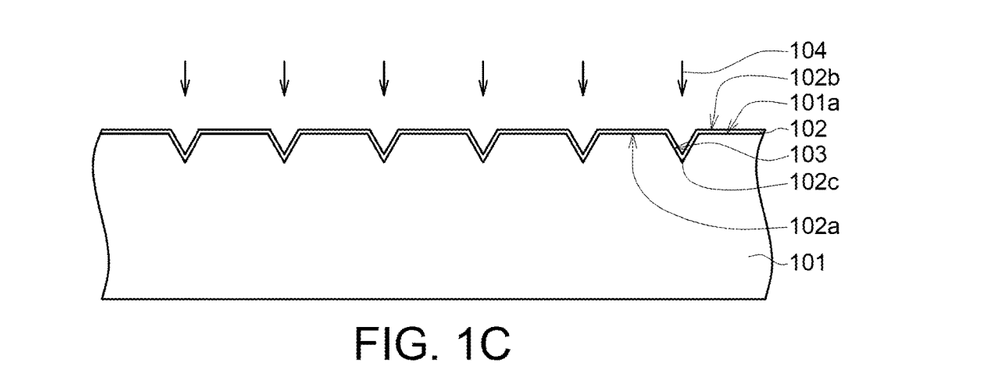

In step S3, an interface layer 102 is formed by the deposition process 104 to cover the surface 101a of the polymer layer 101 and fill the recesses 103. The interface layer 102 has a first surface 102a and a second surface 102b opposite to the first surface 102a. The first surface 102a is in contact with the polymer layer 101 and extends into the recesses 103 of the polymer layer 101, so as to form a plurality of protrusion portions 102c extending into the recesses 103 (as indicated in FIG. 1C). Since the interface layer 102 is conformally in contact with the polymer layer 101 and covers the surface 101a of the polymer layer 101, each protrusion portion 102c also has an aspect ratio substantially ranging from 1 µm to 4000 µm.

The shape and configurations of the protrusion portions 102c are arranged in corresponding to that of the recess 103. For example, the protrusion portions 102c can be arranged in a regular or an irregular manner according to the arrangement of the micro-structures on the surface 101a of the polymer layer 101. Each protrusion portion 102c can be shaped according to the shape of the opening of the corresponding recess 103. For example, the shape of the protrusion portion 102c can be an island structure, a tooth structure, a barb structure, a dove-shaped groove structure, a columnar structure or a combination thereof.

The deposition process 104 may comprise (but is not limited to) physical vapor deposition, chemical vapor deposition, electroplating, electroless plating, powder plasma spraying, laser powder deposition, casting, curing colloidal solution or a combination thereof. The interface layer 102 can be a single- or multi-layered structure. For example, in some embodiments of the present invention, the interface layer 102 comprises at least one layer of metal film formed of titanium (Ti), titanium alloy (Ti-6Al-4V), cobalt-chromium alloy (Co—Cr), stainless steel (SUS 316L), gold (Au), or a combination thereof.

The thickness of the interface layer 102 substantially ranges from 30 µm to 500 µm. In some embodiments of the present invention, the thickness of the interface layer 102, measured from the surface 101a of the polymer layer 101, is greater than 150 µm. In the present embodiment, the interface layer 102 is formed by using a high power ion plating process (such as arc ion plating process) in conjunction with the synthetic powder granulation technology. A low temperature (such as 150° C.) air plasma spray (APS) is performed using a titanium metal powder as a starting material to form at least one layer of titanium metal coating on the surface 101a of the polymer layer 101. In an exemplary embodiment of the present invention, at least one layer of titanium metal film having a thickness substantially greater than 1 µm can be formed on the surface 101a of the polymer layer 101 by way of gradual plating.

Since the atoms of the titanium metal have smaller particles, the heat required for forming high ionized (>90%) particles with high energy (>20 eV) during the melting process can be reduced. Therefore, the surface temperature (<120° C.) of the polymer layer 101 during the plating process can be reduced, the damage of the polymer layer 101 caused by impact of the melting powder colliding with the surface 101a of the polymer layer 101 can be reduced, and the adhesion between the interface layer 102 and the polymer layer 101 can be enhanced.

Moreover, the interface layer 102 can act as a thermal dissipation layer and a buffer layer to avoid the heat generated by the subsequent processes from being accumulated on the surface 101a of the polymer layer 101. When the thickness of the interface layer 102 reaches a certain level, such as greater than 150 µm, the temperature on the surface 101a of the polymer layer 101 can be reduced under the melting point during the subsequent processes, so as to avoid the thermal stress concentrated in subsequent process from penetrating and damaging the polymer layer 101. Besides, since the titanium metal film is conformally in contact with and fills the recesses 103 of the polymer layer 101, thus the plurality of protrusion portions 102c formed in the recesses 103 can have controllable and uniform dimensions to uniformly reduce the residual stress applied on the polymer layer 101 via the interface layer 102 and to avoid the interface layer 102 and the polymer layer 101 from being peeled off by an external force.

Figure 1D:
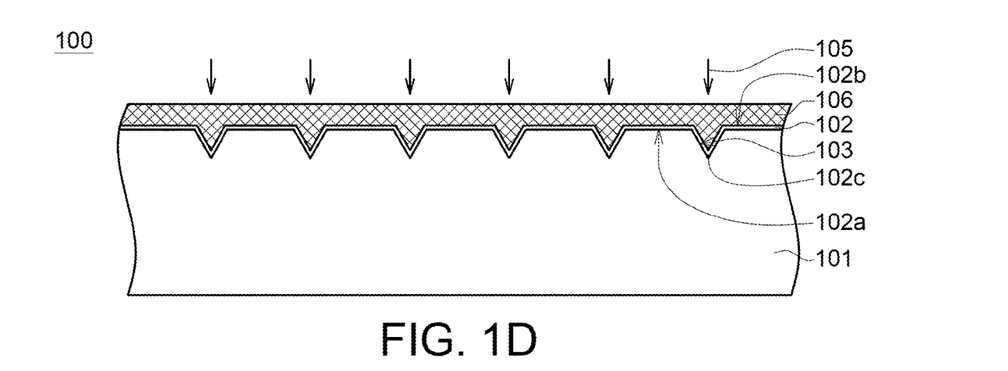

In step S4, a surface plating process is performed on the second surface 102b of the interface layer 102 to form a metal layer 106 (as indicated in FIG. 1D) and complete the preparation of the medical composite material 100. In an exemplary embodiment of the present invention, the surface plating process can be a metal melting process, comprises: guiding an energy beam 105 (comprising the power sources, such as laser beam, electron beam, arc, plasma, electromagnetic conduction or the combination thereof) to smelt metal powder by way of sintering, melting and solidification or a combination thereof, so as to form a porous array metal structure on the second surface 102b of the interface layer 102. The interface layer has a thickness substantially ranging from 30 μm to 500 μm. The metal powder may comprise titanium, gold, silver, iron or a combination thereof. The sintering process can be a selective laser sintering (SLS) process or a direct metal laser sintering (DMLS) process. The melting process can be a selective laser melting (SLM) process or an electron beam melting (EBM) process.

Figure 2:
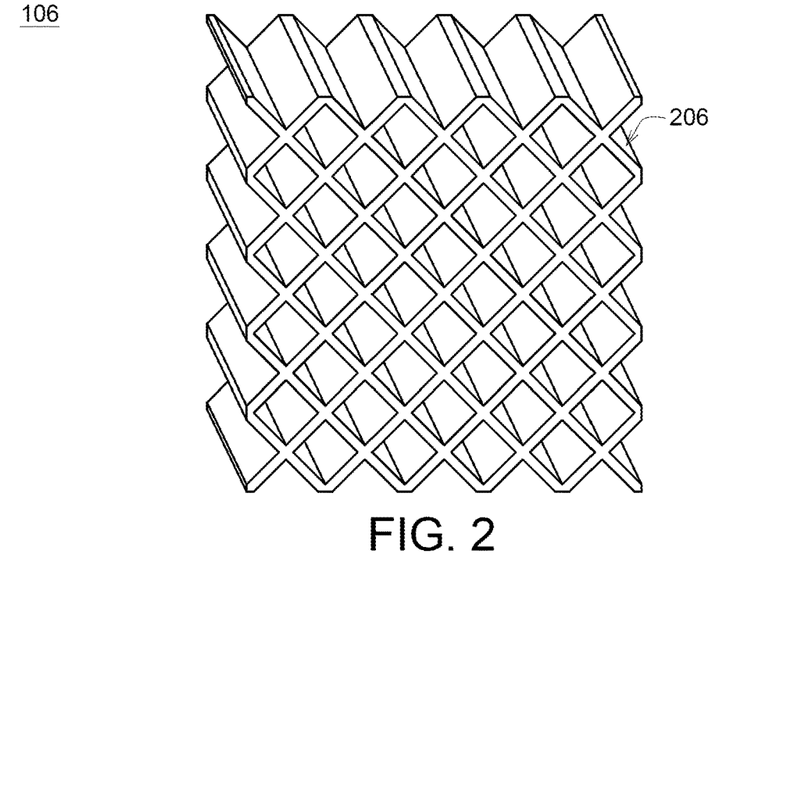

In an exemplary embodiment of the present invention, the porous array metal structure of the metal layer 106 can be a metal mesh structure 206 as shown in FIG. 2. Although the metal mesh structure 206 depicted in FIG. 2 is illustrated as a multi-layered structure in the present embodiment, the metal mesh structure 206 can be a single-layered structure in other embodiments. Since the metal layer 106 has superior biocompatibility for inducing tissue cells to grow on the metal mesh structure 206, thus the metal layer 106 can be tightly fused with the tissues in which it is implanted.

Figure 3A:
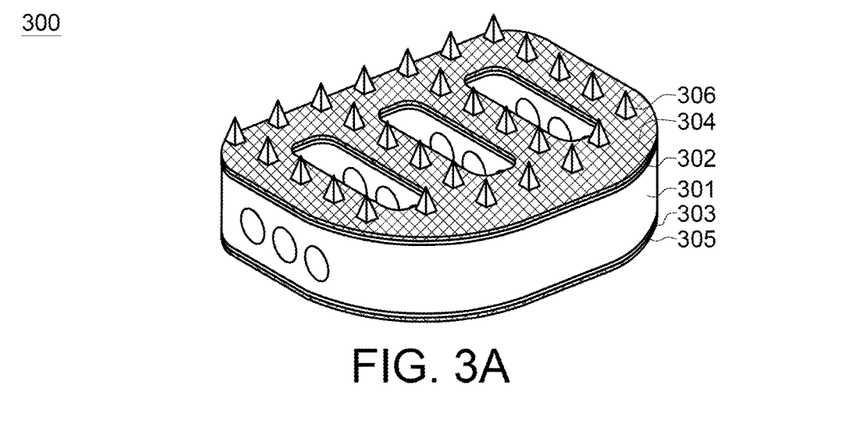
Figure 3B:
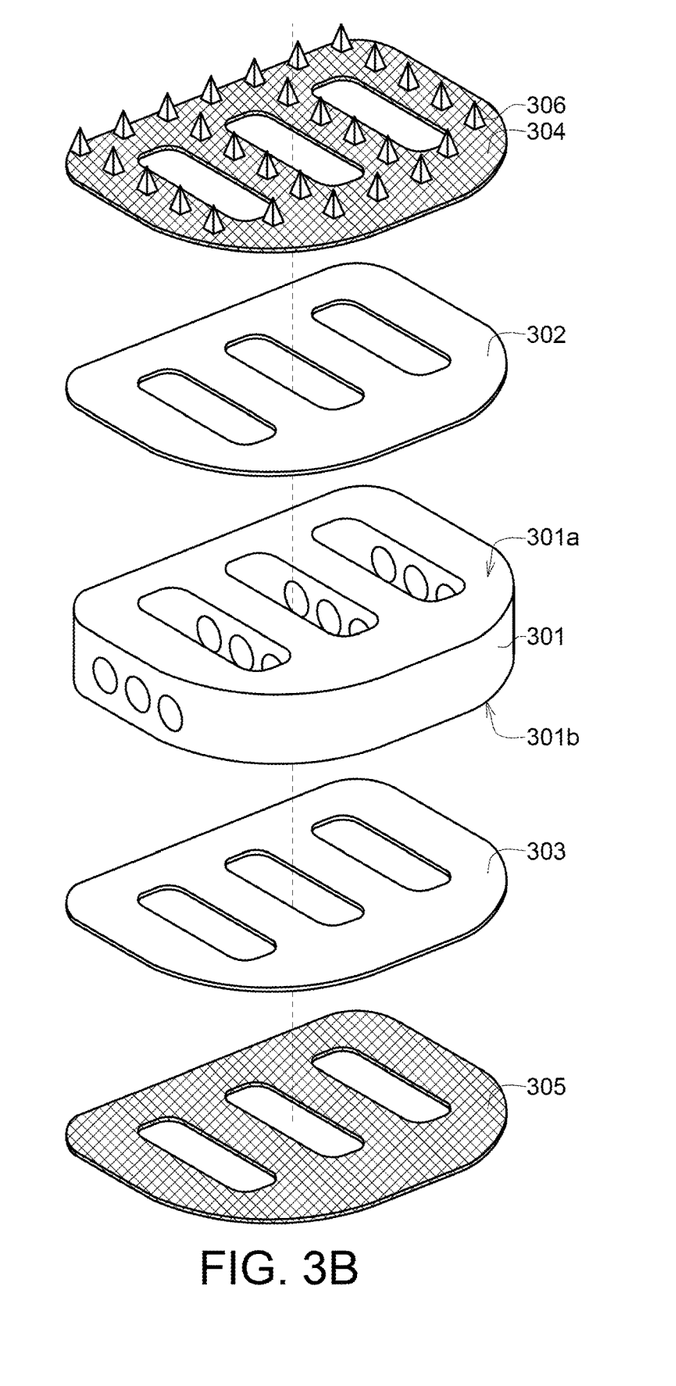

Exemplarily but not restrictively, the medical composite material 100 fabricated by the above method can be used in such as bone screws, spinal fixation device, inter-body fusion device, artificial disk and artificial joints. Refer to FIG. 3A and FIG. 3B. FIG. 3A is a 3D structural perspective of an inter-body fusion device using the medical composite material 100 according to an embodiment of the present invention. FIG. 3B is a structural explosion diagram of the inter-body fusion device 300 of FIG. 3A. The inter-body fusion device 300 comprises a body 301, a first interface layer 302, a second interface layer 303, a first osseo-integration layer 304 and a second osseo-integration layer 305.

The body 301 at least comprises the medical composite material 100 which constitutes the polymer layer 101. For example, in some embodiments of the present invention, the body can be a bulk formed of a material identical to that for forming the polymer layer 101. In some embodiments of the present invention, the body 301 can be a carrying substrate formed of other materials, and the polymer layer 101 is fixed on the top surface and the bottom surface of the carrying substrate (not illustrated) by way of attachment, latching, thermal pressing, or assembly using fasteners, slide slots, bolts, and screw locks. In the present embodiment, the body 301 is a bulk formed of a polymer comprising polyether ether ketone (PEEK), and has an elastic modulus similar to human bone tissues. Thus when the medical composite material 100 is applied to human bone tissues the problems derived from stress shielding effect can be avoided.

The first interface layer 302 and the second interface layer 303, respectively formed on the surfaces 301a and 301b of the body 301 serving as the interface layer 102 of FIG. 1D, are tightly bonded to the body 301, and act as a thermal dissipation layer and a buffer layer to avoid the polymer layer 101 of the body 301 from being damaged by the thermal stress generated by the subsequent processes. In the present embodiment, the structure, materials and formation method of the first interface layer 302 and the second interface layer 303 are exactly the same as that of the interface layer 102 of the medical composite material 100, and the similarities are not redundantly repeated here.

The first osseo-integration layer 304 and the second osseo-integration layer 305 are respectively formed outside the first interface layer 302 and the second interface layer 303, whereby the first interface layer 302 is disposed between body 301 and the first osseo-integration layer 304, and the second interface layer 303 is disposed between the body 301 and the second osseo-integration layer 305. In the present embodiment, since the structures, materials and formation method of the first osseo-integration layer 304 and the second osseo-integration layer 304 are exactly the same as that of the metal layer 106 of the medical composite material 100, thus the first osseo-integration layer 304 and the second osseo-integration layer 305 can be directly sintered (melted) and cured on the first interface layer 302 and the second interface layer 303 to form a one-piece structure with the body 301.

Figure 4:
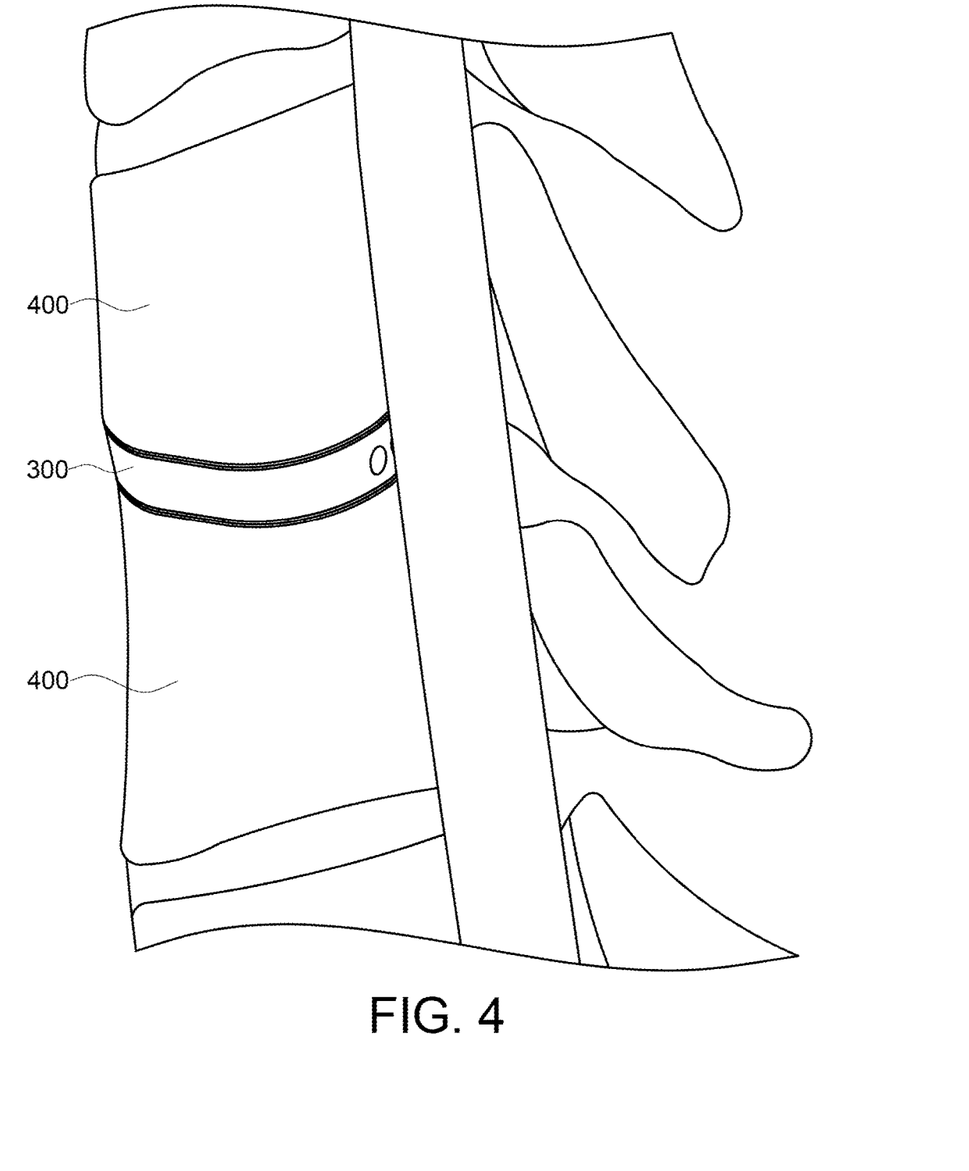

Referring to FIG. 4, a structural diagram of the inter-body fusion device 300 of FIG. 3 used in human vertebrae 400 according to an embodiment of the present invention is shown. The intervertebral disc 300 is implanted between two adjacent vertebrae 400. In some embodiments of the present invention, the inter-body fusion device 300 further comprises a plurality of occlusal teeth 306 disposed on a surface of the first osseo-integration layer 304 and the second osseo-integration layer 305 away from the first interface layer 302 and the second interface layer 303 for improving the security of the inter-body fusion device 300 implanted between the two adjacent vertebrae 400.

In addition, a porous structure, a gradient porous structure, an inducing growth structure, a bionic structure, a physical structure, an increasing friction coefficient structure, a anti-wear structure, a gradient characteristic structure or a combination thereof (not illustrated) suitable for blood and cells attached thereon can be formed on the surface of the occlusal teeth 306 by a surface treatment technology to prompt the fusion between the artificial intervertebral disc 300 and the vertebra.

In accordance with the above disclosure, the embodiments of the present invention disclose a medical composite material with hetero-junction, a method for fabricating the same and applications thereof are disclosed. Firstly, an interface layer 102 is formed on the polymer layer 101 for contacting the polymer layer 101, wherein the interface layer 102 has a plurality of protrusion portions extending into the polymer layer and each protrusion portion has an aspect ratio substantially ranging from 1 μm to 4000 μm. Then, a metal layer with a porous array metal structure is sintered (melted) and cured on the interface layer.

Since the interface layer 102 can be formed on the polymer layer 101 by a low temperature plating technology to avoid the thermal stress concentrated in the subsequent processes from penetrating and damaging the polymer layer 101, thus heterogeneous materials, such as a metal layer and a polymer layer, can be bonded together, and the medical composite material 100, which approximates the nature of human tissues and has excellent developable properties and biocompatibility, can be fabricated.

The medical composite material 100 can be used in the inter-body fusion device 300 for inducing bone cells to grow, such that the inter-body fusion device 300 can be integrated with adjacent vertebrae 400 without peeling off. Moreover, since the polymer material and the adjacent vertebrae has similar elastic modulus, thus stress shielding effect occurs on the prior art medical material that is formed of one single material can be avoided. As a result, the problems encountered in generally known technology can be resolved.

It will be apparent to those skilled in the art that various modifications and variations can be made to the disclosed embodiments. It is intended that the specification and examples be considered as exemplary only, with a true scope of the disclosure being indicated by the following claims and their equivalents

What is claimed is:

1. A medical composite material, comprising:
   an interface layer having a first surface, a second surface opposite to the first surface and a plurality of protrusion portions, wherein each of the protrusion portions protrudes outwards from the first surface, and has an aspect ratio ranging from 1 to 4000; wherein the interface layer is a metal film formed of titanium (Ti), gold (Au), Ti-6Al-4V, Co—Cr, SUS 316L or a combination thereof and having a thickness ranging from 150 µm to 500 µm;
   a polymer layer conformally in contact with the first surface and the protrusion portions; and
   a metal layer in contact with the second surface, wherein the metal layer comprises at least one porous array metal structure comprising at least one metal mesh structure having a thickness ranging from 10 µm to 5000 µm.

2. The medical composite material according to claim 1, wherein a surface of the polymer layer has a plurality of recesses, and the interface layer covers the surface of the polymer layer and extends to the recesses to form the protrusion portions in the recesses.

3. The medical composite material according to claim 1, wherein the polymer layer has an elastic modulus ranging from 2 GPa to 22 GPa.

4. The medical composite material according to claim 3, wherein the polymer layer comprises polyetheretherketone (PEEK), carbon reinforced PEEK, polyetherketoneketo (PEKK), polyaryletherketone (PAEK) or a combination thereof.

5. The medical composite material according to claim 1, wherein the metal mesh structure comprises titanium.

6. A method for fabricating a medical composite material, wherein the method comprises following steps of:
   providing a polymer layer;
   forming an interface layer on the polymer layer, wherein the interface layer has a first surface and a second surface opposite to the first surface, the first surface is conformally in contact with the polymer layer and has a plurality of protrusion portions each extending into the polymer layer and having an aspect ratio ranging from 1 to 4000; wherein the interface layer is a metal film formed of titanium (Ti), gold (Au), Ti-6Al-4V, Co—Cr, SUS 316L or a combination thereof and having a thickness ranging from 150 µm to 500 µm; and
   forming a metal layer on the second surface, wherein the metal layer comprises at least one porous array metal structure comprising at least one metal mesh structure having a thickness ranging from 10 µm to 5000 µm.

7. The method for fabricating a medical composite material according to claim 6, further comprising performing a surface roughening process on a surface of the polymer layer to form a plurality of recesses each having an aspect ratio ranging from 1 to 4000, and then forming the interface layer on the surface.

8. The method for fabricating a medical composite material according to claim 6, wherein the step of forming the interface layer comprises performing a deposition process on the surface of the polymer layer to form the metal film layer extending into the recesses.

9. The method for fabricating a medical composite material according to claim 6, wherein the step of forming the metal layer comprises a surface plating process.

10. The method for fabricating a medical composite material according to claim 9, wherein the surface plating process is a metal melting process, which comprises guiding an energy beam to perform a sintering curing process, a melting curing process or a combination thereof on a metal powder to form a porous array structure on the second surface.

11. An inter-body fusion device, comprising:
    an interface layer having a first surface, a second surface opposite to the first surface and a plurality of protrusion portions each of which protrudes from the first surface and has an aspect ratio substantially ranging from 1 µm to 4000 µm; wherein the interface layer is a metal film formed of titanium (Ti), gold (Au), Ti-6Al-4V, Co—Cr, SUS 316L or a combination thereof and having a thickness ranging from 150 µm to 500 µm;
    a body comprising a polymer layer conformally in contact with the first surface and the protrusion portions; and
    an osseo-integration layer comprising a metal layer and in contact with the second surface, wherein the metal layer comprises at least one porous array metal structure comprising at least one metal mesh structure having a thickness ranging from 10 µm to 5000 µm.

* * * * *